US 9,592,180 B2

(12) United States Patent
Weinstein et al.

(10) Patent No.: US 9,592,180 B2
(45) Date of Patent: Mar. 14, 2017

(54) METHOD AND DEVICE FOR TREATING ALLERGIC REACTIONS AND DIFFICULT-TO-MANAGE RESPIRATORY DISEASES

(71) Applicant: Pharmaceutical Design, LLC, Potomac, MD (US)

(72) Inventors: Allan M. Weinstein, Potomac, MD (US); Robert E. Weinstein, Miami, FL (US)

(73) Assignee: Pharmaceutical Design, LLC, Potomac, MD (US)

( * ) Notice: Subject to any disclaimer, the term of this patent is extended or adjusted under 35 U.S.C. 154(b) by 0 days.

(21) Appl. No.: 14/671,629

(22) Filed: Mar. 27, 2015

(65) Prior Publication Data

US 2016/0136049 A1    May 19, 2016

Related U.S. Application Data

(60) Provisional application No. 61/933,549, filed on Jan. 30, 2014.

(51) Int. Cl.
*A61J 1/16* (2006.01)
*A61M 15/00* (2006.01)
(Continued)

(52) U.S. Cl.
CPC .............. *A61J 1/16* (2013.01); *A61K 31/137* (2013.01); *A61M 5/002* (2013.01); *A61M 15/00* (2013.01); *B65D 25/04* (2013.01); *B65D 25/205* (2013.01); *B65D 43/02* (2013.01); *A61M 15/009* (2013.01); *A61M 15/0045* (2013.01); *A61M 2202/064* (2013.01); *A61M 2205/581* (2013.01); *A61M 2205/583* (2013.01);
(Continued)

(58) Field of Classification Search
CPC ......... A61F 17/00; A61B 19/02; A61B 50/00; A61B 50/20; A61B 50/30; A61B 2050/3008; A61J 1/16; B65D 25/04; B65D 25/205; B65D 43/02
USPC .......................... 206/570, 223, 438, 571, 572
See application file for complete search history.

(56) References Cited

U.S. PATENT DOCUMENTS 4,501,363 A * 2/1985 Isbey, Jr. ...................... 206/363
4,522,302 A * 6/1985 Paikoff ................. A61M 5/003
                                               206/216
(Continued)

OTHER PUBLICATIONS

PCT International Search Report and Written Opinion, PCT/US2015/023287, mail date Jun. 29, 2015.

*Primary Examiner* — Steven A. Reynolds
(74) *Attorney, Agent, or Firm* — Robert R. Deleault, Esq.; Mesmer & Deleault, PLLC

(57) ABSTRACT

A medication treatment kit to ensure administration of medications in proper order for a treatment protocol requiring that the medications be taken in a particular order has a container, a lower tray or drawer located in a lower portion of the container, the lower tray or drawer containing a second-line treatment medication for a particular treatment protocol wherein the second-line treatment medication is not to be taken first by the user, and an upper tray located in an upper portion of the container, the upper tray containing a first-line treatment medication required to be taken first by the user whereby the kit has a configuration that ensures the first-line medication is used first.

14 Claims, 9 Drawing Sheets

(51) Int. Cl.
    *A61M 5/00*         (2006.01)
    *A61K 31/137*     (2006.01)
    *B65D 25/04*      (2006.01)
    *B65D 25/20*      (2006.01)
    *B65D 43/02*      (2006.01)

(52) U.S. Cl.
    CPC .............. *A61M 2205/6009* (2013.01); *A61M 2205/6045* (2013.01); *A61M 2209/06* (2013.01)

(56) References Cited

U.S. PATENT DOCUMENTS

| | | | |
|---|---|---|---|
| 4,595,102 A * | 6/1986 | Cianci | A61B 19/0271 206/370 |
| 4,736,850 A * | 4/1988 | Bowman | A61F 2/062 206/370 |
| 5,392,917 A * | 2/1995 | Alpern | B65D 77/2056 206/370 |
| 5,931,304 A * | 8/1999 | Hammond | A61F 17/00 206/425 |
| 5,979,658 A * | 11/1999 | Allen | A61F 17/00 206/223 |
| 6,012,586 A * | 1/2000 | Misra | 206/370 |
| 7,100,771 B2 * | 9/2006 | Massengale | A61M 5/002 206/363 |
| 7,806,265 B2 * | 10/2010 | Timm | A61K 9/0048 206/363 |
| 2003/0121821 A1 * | 7/2003 | Roshdy | A61B 19/0271 206/570 |
| 2005/0085799 A1 | 4/2005 | Luria et al. | |
| 2005/0172961 A1 | 8/2005 | Nesbitt | |
| 2009/0136599 A1 | 5/2009 | De Amorim | |
| 2010/0274205 A1 * | 10/2010 | Morelli | A61M 1/0088 604/290 |
| 2012/0185276 A1 * | 7/2012 | Shah | A61M 15/009 705/3 |
| 2013/0292294 A1 * | 11/2013 | Wilson | A61F 17/00 206/571 |
| 2014/0224704 A1 * | 8/2014 | Bertazzoni | A61B 19/02 206/570 |
| 2015/0014211 A1 * | 1/2015 | Nickell | A61F 17/00 206/572 |
| 2015/0027922 A1 * | 1/2015 | Fresco | A61F 17/00 206/570 |

\* cited by examiner

METHOD AND DEVICE FOR TREATING ALLERGIC REACTIONS AND DIFFICULT-TO-MANAGE RESPIRATORY DISEASES

BACKGROUND OF THE INVENTION

1. Field of the Invention

The present invention relates generally to methods and devices for treating allergic reactions as well as difficult-to-manage respiratory and other difficult-to-manage diseases. Particularly, the present invention concerns a method and device for organizing, storing and coordinating emergency medications, thereby removing the confusion associated with the treatment of anaphylaxis, a potentially life-threatening event, as well as for the treatment of difficult-to-manage allergies and respiratory diseases including asthma.

2. Description of the Prior Art

Allergies are an overreaction of the body's natural defense system—this natural defense system is known as the immune system. The immune system normally protects the body from viruses and bacteria, for example, by producing antibodies to fight them. One usually thinks of antibodies as the body's defense system for fighting infection. However, in an allergic reaction, the immune system starts fighting substances that are usually harmless such as dust mites, pollen, or a medicine as though these substances were trying to attack the body. This overreaction can cause a rash, itchy eyes, a runny nose, trouble breathing or swallowing, nausea, and diarrhea.

An allergic reaction may not occur the first time you are exposed to an allergy-producing substance called an allergen. For example, the first time a person is stung by a bee, that person may have only pain and redness from the sting—the first exposure to an allergen (such as bee venom, a food or medication) is called sensitization. However, if the person is stung again, the person may have hives or trouble breathing. This is caused by the response of the immune system called an IgE-immediate-type reaction. In summary, a person is not born with allergies, just the tendency to develop allergies. Allergies develop with exposure over time and IgE antibodies develop to the specific allergen. On re-exposure to the allergen, symptoms can result that involve the nose (hayfever or allergic rhinitis), the eyes (allergic conjunctivitis), the skin (hives and eczema), as well as the airways (asthma).

Most people will have some problem with allergies or allergic reactions at some point in their lives. Allergic reactions can range from mild and annoying (such as runny nose and sneezing) to sudden and potentially life-threatening. Most allergic reactions are mild and home treatment with over-the-counter medications can relieve many of the symptoms. If symptoms are more severe or persistent, or cause breathing problems such as asthma, a doctor visit is required for evaluation and prescription treatments that can be organized for the patient into a treatment plan. The most severe allergic reaction, called anaphylaxis, can trigger immediate allergic responses such as hives, difficulty swallowing, gastrointestinal symptoms (including diarrhea, vomiting, and abdominal cramps), and breathing problems such as asthma, as well as a drop in blood pressure.

Allergies often occur along with other diseases, such as asthma, ear infections, sinusitis, and sleep apnea. There are many types of allergies. Some of the more common allergens include inhaled pollens (such as ragweed, tree, or grass), dust, molds, foods (such as peanuts, seafood, eggs and milk), medicines (such as penicillin), insect venom (bee stings), animals (cats, dogs, and horses), or natural rubber. Food allergies are most common in people who have an inherited tendency to develop allergic conditions. These people are more likely to have asthma and other allergies. Many prescription and nonprescription medicines can cause an allergic reaction. Allergic reactions are common and unpredictable. The seriousness of the allergic reaction caused by a certain medicine will vary.

Insect bites/stings typically include poisons and other toxins in the insect's bite and/or venom that enter the skin. It is normal to have some swelling, redness, pain, and itching at the site of a bite/sting. An allergic reaction to the bite/sting occurs when the body's immune system overreacts to the venom of biting/stinging insects. Allergies to animals are more likely to cause breathing problems than skin problems. The allergy may be caused by a pet's dead skin (dander), urine or dried saliva. Some people develop allergic reactions after repeated contact with latex, especially latex gloves. Other causes of severe allergic reactions or anaphylaxis include hormones, antisera, insulin, allergy immunotherapy (allergen extracts), and exercise. Non-allergic causes can also trigger similar severe symptoms; classified as anaphylactoid reactions because they are not caused by an IgE-mediated response, they can include reactions to aspirin, nonsteroidal anti-inflammatory medications (such as ibuprofen), opiates, radiocontrast media used for diagnostic scans, and certain anaesthetics.

When a severe systemic allergic reaction resulting from exposure to allergens is rapid in onset, such a reaction is called anaphylaxis. In some cases, anaphylaxis can cause death. Anaphylaxis typically involves body organ systems. The degree of involvement varies among patients, and even in the same patient from one reaction to another. There are general patterns, however, regarding organ system involvement. The organ systems that exhibit anaphylaxis symptoms include the skin (80% to 90% of reactions), respiratory tract (70% of reactions), gastrointestinal tract (30% to 45% of reactions), cardiovascular system (10% to 45% of reactions), and central nervous system (10% to 15% of reactions). Symptoms involving the throat, lung, or cardiovascular system can potentially be life threatening.

Anaphylaxis often produces signs and symptoms within minutes of exposure to an allergen. Some reactions, however, may develop later (more than 30 minutes after exposure) and symptoms not immediately life-threatening can progress rapidly and become potentially life-threatening unless promptly treated. In some cases, a second reaction, called a delayed reaction, occurs 1 to 72 hours (usually within 8 hours) after initial recovery despite no further exposure to the trigger.

Thus, anaphylaxis is a potentially life-threatening allergic reaction. Symptoms typically come on quite suddenly, within minutes or even seconds, and can range from a sensation of warmth with flushing, itchiness, anxiety, raised red patches (urticaria or hives), swelling which can be severe (angioedema), stomach pain, to difficulty breathing with wheezing and cough (especially for asthma sufferers), difficulty swallowing, as well as a feeling that one is passing out (due to a drop in blood pressure which can lead to cardiovascular collapse and shock). When swelling occurs around the mouth and lips (called angioedema), it can be quite disfiguring; when swelling occurs in the upper airways or throat, it can be life-threatening.

Triggers to anaphylaxis can include foods (such as shellfish and peanuts), bee stings, and adverse reactions to exercise or medications (e.g., penicillin, aspirin, and codeine). Anaphylaxis can also occur without known cause or explanation, which is called idiopathic anaphylaxis. Although identifying the symptoms of anaphylaxis would seem to be quite clear-cut, that is not always the case.

Epinephrine is the first-line treatment of life-threatening allergic reactions (anaphylaxis) according to NIH-NIAID Food Allergy guidelines. Epinephrine is the drug found in various auto-injector products sold under the trademarks EpiPen®, EpiPen Jr®, and Allerject™. The drug is delivered intramuscularly (IM) or subcutaneously (SC) into the outer thigh. A second injection may be necessary as patients often have ongoing symptoms unresolved with the first dose. It is for this reason that these products are often dispensed in packs of two. During a life-threatening allergic reaction (anaphylaxis), epinephrine quickly begins working to reverse symptoms of a life-threatening allergic reaction (anaphylaxis) by constricting blood vessels to increase blood pressure, relaxing smooth muscles in the lungs to reduce wheezing to improve breathing, stimulating the heart (increasing heart rate), and working to reduce hives as well as swelling that may occur around the face and lips. Epinephrine is also used as an emergency medication for severe asthma, unrelated to an anaphylactic event.

Adjunctive medications include H1 antihistamines—such as diphenhydramine (Benadryl) or chlorpheniramine—and H2 antihistamines—such as cimetidine (Tagamet) or ranitidine (Zantac), which are often used together, as well as inhaled beta-agonists (albuterol) for shortness of breath due to asthma symptoms. Oral corticosteroids are often given to prevent delayed onset of anaphylactic symptoms.

Current practice for treating a life-threatening allergic reaction includes administering epinephrine and then being immediately transported to a hospital. There are situations, however, where going immediately to a hospital is not possible.

SUMMARY OF THE INVENTION

Allergy and asthma sufferers have an array of medications to control their symptoms—antihistamines such as diphenhydramine (Benadryl®), chlorpheniramine (Chlor-Trimeton®), loratadine (Claritin®), fexofenadine (Allegra®), and citirizine (Zyrtec®); nasal inhalers such as Flonase® and Nasonex®, asthma medications such as asthma rescue inhalers albuterol (Ventolin® or Proventil®); asthma preventive inhalers such as Advair®, Symbicort®, Flovent®, and pills such as Singulair®. One or more of these medication types may be used routinely, while others are used on an as-needed basis when symptoms arise. Allergy sufferers are routinely required to determine on their own whether they need to add an additional medication to their routine medications. It is when facing these routine decision-making events that an anaphylactic episode can quickly occur. However, it must be emphasized that only a small percentage of allergy sufferers seek physician care—less than 5% see an allergist. These allergy sufferers turn to the over-the-counter market for medications and to their family physician or to the emergency room when symptoms arise. It is for this reason that the very medications that patients use routinely for allergy and asthma can serve to distract the patient who is experiencing an anaphylactic episode away from using epinephrine, the first-line medication, which requires an injection. The use of adjunctive medications, such as antihistamines, an immediate-onset asthma inhaler, and prednisone have an important but secondary role in treatment as well.

Many allergy specialists believe that epinephrine should be widely available in schools and in the work place. Some specialists believe that every household should have an epinephrine auto-injector at home, as the incidence of food allergy is on the rise and a severe bee sting reaction is unpredictable. It is the object of this invention to organize the medications that patients might turn to in a way that immediately directs them to epinephrine as the first-line alternative. Delay in administering epinephrine can increase the risk of a life-threatening reaction. Every asthma and allergy sufferer should carry the device when traveling to ensure that they have the appropriate medications in case of an anaphylactic episode or a severe asthma attack.

Although there are some devices that have auto-injection instructions directed to the user (Auvi-Q®), there is great need to combine more personalized, real-time instruction that is tied in with the newest information technologies available (such as electronic medication history reconciliation from pharmacies and payers, electronic medical records, and patient electronic health records). There is a further need to have epinephrine available and to locate the nearest epinephrine using locating systems currently available or those that will be further invented.

Confusion occurs routinely as patients often believe that they are experiencing an allergic reaction that will pass with time or simply having a bad asthma day, and turn to their prescribed antihistamine or asthma inhaler as a first-line approach. With skin symptoms as the presenting symptom, the use of an antihistamine can be temporarily and misleadingly helpful, thereby delaying definitive treatment. The use of these routine medications, with the hope that these medications will suffice, unfortunately puts the patient at great risk. Delay in seeking emergency medical treatment due to the confusing range of symptoms associated with anaphylaxis, and due as well to the range of medications that patients have at their disposal as first-line alternatives to epinephrine, increases risk, as the definitive treatment of anaphylaxis is to take an epinephrine injection as soon as possible.

When facing these varying symptoms that occur quite abruptly (with or without a clear-cut cause) and that sometimes begin with or seem like routine symptoms for those with underlying conditions (asthma and urticaria, as examples), the anaphylaxis-sufferer and those around them (e.g., family members, schools, co-workers) need to react immediately in selecting emergency medications and proceeding for emergency treatment.

Thus, it is not always possible to know when a life-threatening allergic reaction will occur or the triggers that set off such an allergic reaction. In addition, someone suffering from anaphylaxis may not be able to immediately go to a hospital (for example, when in a remote location).

It is an objective of the present invention to provide a method and device for treating difficult-to-manage diseases that require that medication be administered in a particular order for the treatment to be effective.

There is a compelling need for treatment methods, technology and packaging devices that address confusion and incorrect order of administration of medications. It is an objective of the present invention to make certain that the first-line medication is used first by a patient having a difficult to treat disease followed by the second-line medication. It is another objective of the present invention to reduce medication selection errors and to insure that the first-line use of the proper medication is taken, followed by the adjunctive or second-line medication.

There is clearly a compelling need for emergency anaphylaxis treatment methods, technology and packaging devices that address this confusion and directs the patient to the proper medication and the emergency room. It is not sufficient to rely on epinephrine alone, as persistent or delayed symptoms may occur, thus necessitating the need to locate and find the nearest emergency room. In addition, if emergency care is not nearby or if an additional dose of epinephrine is needed, technology to locate a pharmacy or an epinephrine device itself can be life-saving. Although patient education in the physician's office is important to reinforce the first-line use of epinephrine, it must be emphasized that many patients are reluctant to give themselves an injection even with an auto-injector. Although it might seem that patient education alone is the answer, this is not the case.

It is the objective of the present invention to make certain that epinephrine is the first-line medication used by a patient experiencing anaphylaxis.

It is another object of the present invention to reduce medication selection errors and to ensure the first-line use of epinephrine in context with adjunctive medications such as antihistamines and an asthma rescue inhaler.

It is another object of the present invention to provide a device and method of treatment that provides a person suffering from a life-threatening allergic reaction sufficient time to get the allergic reaction under control while arranging to get to a hospital. There have been reported incidents where people with asthma suffering anaphylaxis have died even though they were within sight of a hospital emergency room.

The present invention achieves these and other objectives by providing, in one embodiment, a kit having a container containing a first-line medication and a second line medication. The container is configured to present the first-line medication to the user first and then the second-line medication is presented to the user after the user further manipulates the container. The container may include a base unit containing the second-line medication and a removable tray disposed over the second-line medication that contains the first-line medication. The container may optionally include indicia and/or a warning on the removable tray that clearly shows the order of administration of the first-line medication in the removable tray. The base unit may also optionally include indicia and/or a warning that clearly shows the order of administration of the second-line medication. The indicia and/or warning on the base unit are hidden from the user's view until the user removes the removable tray.

In another embodiment, the kit includes a container configured with an upper compartment and a drawer below the upper compartment. Above the drawer in the upper compartment resides the first-line medication. The second-line medication is disposed in the drawer. In the assembled state, the second-line medication is not seen by the user. The upper compartment where the first-line medication is disposed has indicia and/or a warning that clearly shows the order of administration of the first-line medication in the container. The drawer may also optionally include indicia and/or a warning that clearly shows the order of administration of the second-line medication. The indicia and/or warning on the drawer are hidden from the user's view until the user opens the drawer.

In yet another embodiment, the kit includes a container configured with at least one fold-out tray. The container has a base compartment and the folding tray disposed within the container above the base compartment in an assembled state. In a first orientation, the first-line medication and the second-line medication face each other. In a second orientation, the first-line medication and the second-line medication do not face each. This is akin to the orientation of the embodiment with the removable tray with the difference being that the fold-out tray is hingedly attached to the container whereas the removable tray is not. In either orientation, indicia and/or warnings are affixed to the surface of the respective base compartment and/or fold-out tray having access to the respective medication. In both orientations, the indicia and/or warning of the second-line medication are hidden from the user's view until the user opens the container.

In another embodiment, the fold-out tray may optionally include additional fold-out trays where the base compartment or one of the fold-out trays contains the first-line medication while the remaining medication holding compartments has the second-line medication. This embodiment may include a plurality of structure that clearly indicates the first-line medication must be used before using the second-line medication, which structures are described elsewhere in this disclosure.

In one embodiment, the present invention may include an audio message playback module. The audio module provides an audio warning that is activated when (1) the container is opened, or (2) the removable tray is removed from the container in one embodiment, or (3) the drawer of the container is opened in another embodiment, or (4) the fold-out tray is pivoted away from the base compartment in yet another embodiment, etc. The warning reminds the user that the first-line medication must be administered first for proper treatment. The audio warning may also contain further warnings of the danger of administering only the second-line treatment medications or of the possible second and/or delayed reaction.

In one embodiment specific to allergic reactions, the present invention contains two or more epinephrine delivery units front and center when opening the device. There are no other medications side-by-side to confuse the user—adjunctive medications (such as antihistamines and an asthma inhaler) are provided but they are layered below, such that they are available only when epinephrine has first been administered, further re-enforcing the first-line use of epinephrine.

In one embodiment, the present invention is an allergic reaction kit having a plurality of epinephrine auto-injectors, a plurality of dosages of antihistamine, and a rescue inhaler.

As anaphylactic events occur randomly and take place within seconds to minutes, another embodiment of the present invention includes automatic telecommunication capability when opened to (a) immediately communicate with a call center to provide the anaphylaxis sufferer with medical counseling (as the patient may not recall their doctor's office instructions), (b) communicate to the anaphylaxis sufferer the location of the closest emergency room (possibly directing a rescue squad), and (c) direct the user to another epinephrine device in a pharmacy or nearby patient carrying an epinephrine device, if necessary, and (d) communicate directly to the patient's physician and patient portal tied to the patient's electronic medical record or to the electronic medical record itself. This same communication system may be added to a medical alert bracelet or other means of identifying an anaphylaxis sufferer and their specific allergies.

In one embodiment of the present invention, the allergic reaction kit includes a container having a lower compartment and an upper compartment. The lower compartment contains the plurality of dosages of antihistamine and the rescue inhaler. A removable lower seal or sealing member covers the lower compartment. In the upper compartment is a plurality of epinephrine auto-injectors. The plurality of epinephrine auto-injectors are retained in the upper compartment by a removable upper seal. The container also includes a plurality of indicia that visually indicates the medications within the two compartments. The arrangement of the compartments in this embodiment is an important feature of the present invention. The lower compartment is not accessible until the upper compartment is opened. This comports with the method of the invention that teaches application of the epinephrine first as the primary treatment and then administration of the antihistamine and/or rescue inhaler as the secondary treatment. In the preferred embodiment, the antihistamine and the rescue inhaler would be an optional treatment if required. In this embodiment, the removable seals may be made of a flexible, peelable material that is clear, translucent or opaque. A pressure-sensitive adhesive material may be used along the periphery of the seals for attaching the seals to their respective locations in the container. The peelable material may include a means such as a tab to facilitate removal of the seal when accessing the medication within the container.

In another embodiment of the present invention where the container has lower and upper compartments, the removable seal may be made of a rigid or resilient material. The removable seal in this embodiment may also be held in place by a self-adhesive material or may involve mechanical retention devices. The mechanical retention devices may include tape, pivotable retaining tabs or clips, a plurality of frangible connections, and the like. Other mechanical retention devices may include a catch mechanism or a keyed release mechanism.

In still another embodiment of the present invention, the container may have side-by-side compartments. A first compartment would contain the plurality of epinephrine auto-injectors and a second compartment would contain the antihistamine and/or rescue inhaler. This embodiment may also include a plurality of indicia and/or instructions for using this specialized emergency kit. Unlike the prior embodiment where accessing the lower compartment containing the secondary treatment medication requires accessing the upper compartment first, this embodiment requires a mechanism to reduce a user's propensity to by-pass the primary treatment medication and access the secondary treatment medication first. The mechanism contemplated can be as simple as a separate key within the primary treatment medication compartment that "unlocks" the secondary treatment medication compartment. The separate key would only be accessible after opening the primary treatment medication. To further minimize non-use of the primary treatment medication in favor of using the secondary treatment medication, the key may be a component of the epinephrine auto-injector. One example of such a key may be a safety release component of the auto-injection that must be removed before use of the auto-injector or epinephrine syringe. The safety release would have a configuration or structure that unlocks the seal of the second compartment containing the secondary medication. Another example could be associated with a change in the width or length of the auto-injector after its one-time use. The size of the auto-injector after use (i.e. the change in the width or length) would be the key or structure that unlocks the seal of the second compartment for accessing the secondary treatment medication.

In still another embodiment of the present invention, the allergic reaction treatment kit optionally includes automatic telecommunication capability when opened to (a) immediately communicate with a call center to provide the anaphylaxis sufferer with medical counseling (as the patient may not recall their doctor's office instructions), (b) communicate to the anaphylaxis sufferer the location of the closest emergency room (possibly directing a rescue squad), and (c) direct the user to another epinephrine device in a pharmacy or to a nearby patient carrying an epinephrine device, if necessary, and (d) communicate directly to the patient's physician and patient portal tied to the patient's electronic medical record or to the electronic medical record itself. This same communication system can be added to a medical alert bracelet or other means of identifying an anaphylaxis sufferer and their specific allergies. In all instances, all forms of communication will serve to reinforce that epinephrine is the first line of therapy, that it is to be used if the patient has difficulty breathing, difficulty swallowing, or feels faint (the symptoms of analphylaxis), and that the patient must immediately proceed to the nearest emergency room (even if epinephrine has been given).

DETAILED DESCRIPTION

Figure 1:
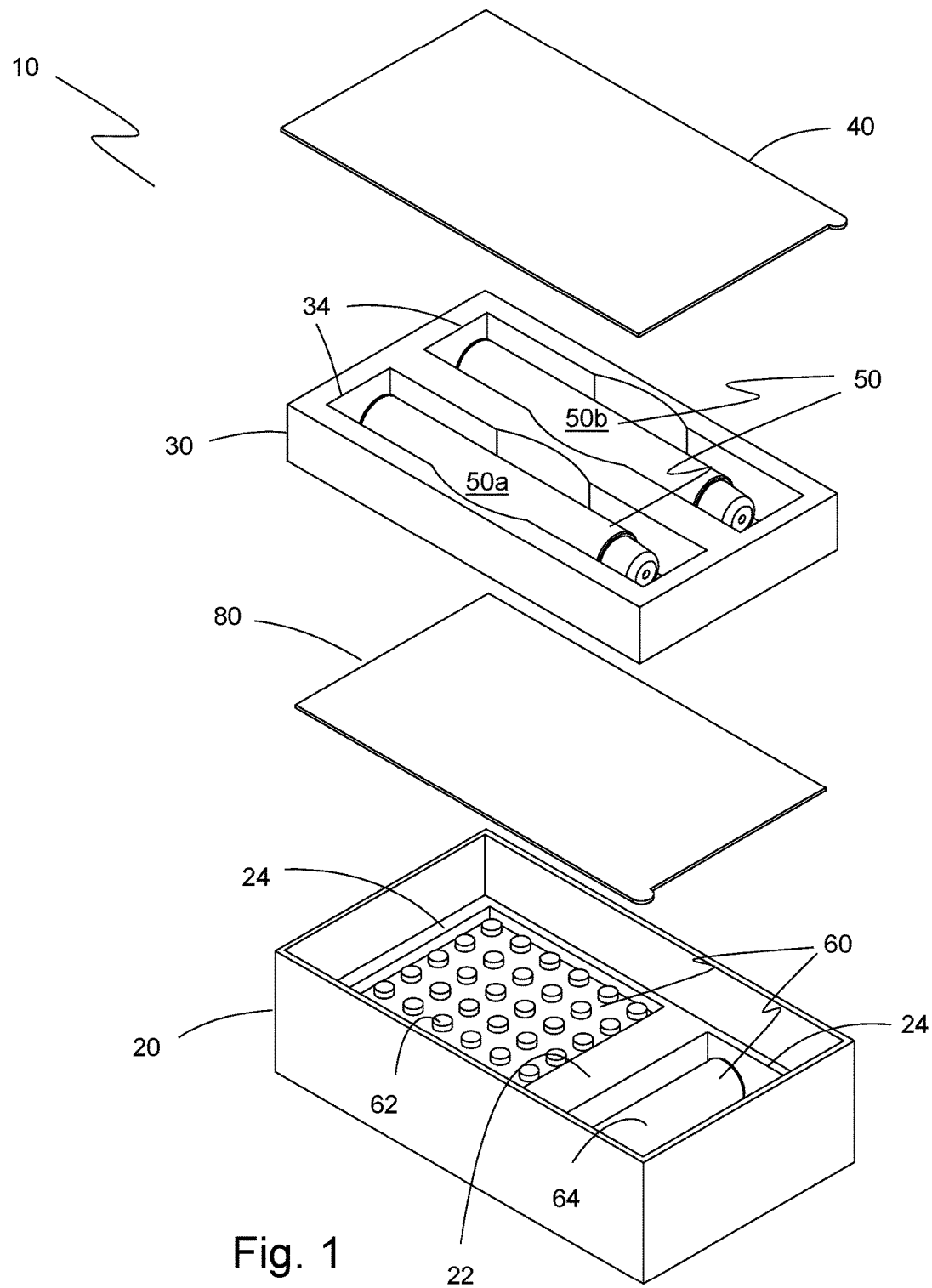
FIG. 1 is a perspective view of one embodiment of the present invention showing a container with layered storage compartments.

The preferred embodiments of the present invention are illustrated in FIGS. 1-9. FIG. 1 shows one embodiment of the allergic reaction treatment kit 10. Treatment kit 10 includes a container 20 having a lower tray 22 containing a second-line treatment medication 60, a removable upper tray 30 containing a first-line treatment medication 50 and a container sealing cover 40. Lower tray 22 has one or more lower compartments 24 for containing one or more second-line treatment medications 60. Upper tray 30 also has one or more upper compartments 34 for containing one or more medications for the first-line treatment medication 50. Container sealing cover 40 retains the first treatment medications 50, the upper tray 30 and the second treatment medications 60 in a sealed environment within container 20 until a person having an allergic reaction requires treatment. Allergic reaction treatment kit 10 may optionally contain instructions 100 for administering the first-line and second-line treatment medications 50, 60, respectively, to a person having a potentially severe allergic reaction known as anaphylaxis. Instructions 100 may be printed on container 20 or on container sealing cover 40 or packaged within or on upper tray 30.

In the present invention, the first-line treatment medication 50 is epinephrine. Upper tray 30 contains a first and a second medication injector 50a, 50b containing epinephrine. The arrangement and accessibility of the first-line treatment medication 50 and the second-line treatment medication 60 is a critical factor in allergic reaction treatment kit 10. Two or more epinephrine delivery units are presented first for administration to a person having a potentially severe allergic reaction when opening the treatment kit 10. There are no other medications side-by-side relative to the first-line medication 50 to confuse the user. Second-line medications 60 are provided but they are layered below first-line medication 50 in treatment kit 10 where only the first-line medication is initially presented to the user so that they are available only when epinephrine has first been administered, further re-enforcing the first-line use of epinephrine.

Treatment kit 10 may also optionally contain a second compartment sealing member 80 that retains second-line medication 60 within lower tray 22. Sealing member 80 may be a single sealing member that seals the plurality of lower compartments 24 or may be a plurality of sealing members where each one seals one of the lower compartments 24. Second-line treatment medication 60 contains medications known as adjunctive medications, such as, for example, antihistamines 62 and an asthma inhaler 64.

Figure 2:
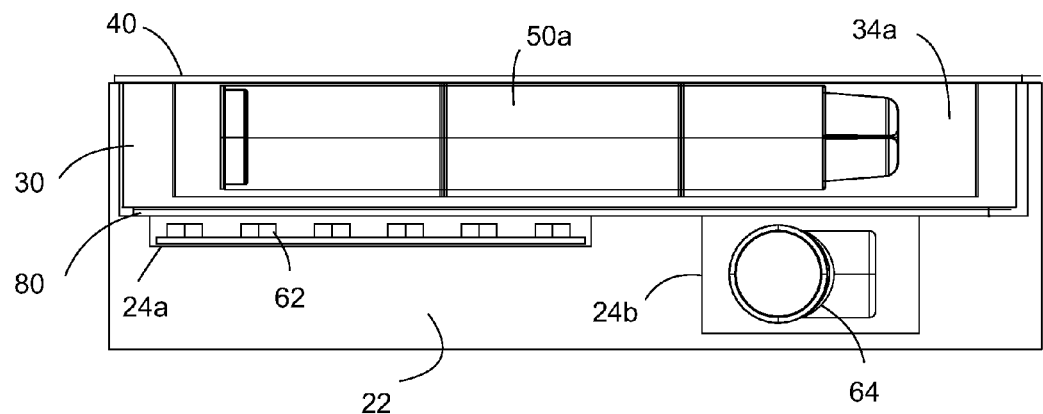
FIG. 2 is a side view of the present invention in FIG. 1.

Turning now to FIG. 2, a side view of the embodiment in FIG. 1 of the present invention is illustrated. Lower tray 22 has two compartments 24a and 24b. Compartment 24a contains a second-line treatment medication 62 that is an antihistamine in pill form in this embodiment. Compartment 24b contains a second-line treatment medication 64 that is an inhaler. Optional sealing member 80 encloses second-line treatment medications 62, 64 within lower tray 22. It is contemplated that lower tray 22 may be a separate, removable tray within container 20 or it may be integrally-formed in container 20.

Removable upper tray 30 is stacked on top of lower tray 22 with or without an intervening sealing member 80. Removable upper tray 30 has two compartments 34a and 34b (shown in FIGS. 1 and 4). Each compartment 34a, 34b contains the first-line treatment medication 50a, 50b, which each one is an epinephrine applicator that is an auto-injector (such as Epi-Pen®, Auvi-Q®, Twin-Jet®) or epinephrine-containing syringe to deliver epinephrine intramuscularly or subcutaneously into the outer thigh. The contents of container 20 are retained within container 20 by container sealing cover 40.

Figure 3:
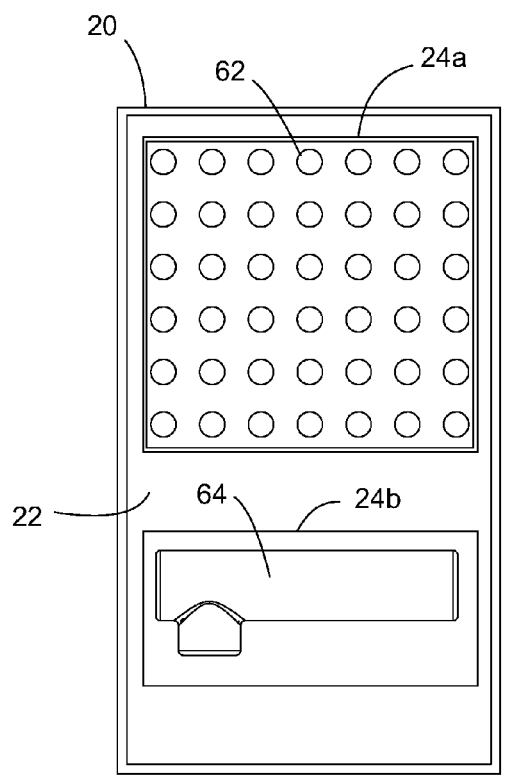
FIG. 3 is a top view of FIG. 1 showing only the lower compartments of the container.

FIG. 3 is a top view of container 20 and lower tray 22 where lower tray 22 may or may not be removable from container 20. An inhaler 64 such as an asthma rescue inhaler is positioned within compartment 24b. A plurality of pills or tablets 62 such as antihistamine (sedating or nonsedating) is positioned within compartment 24a. It is contemplated that the antihistamine may be in another form such as a liquid. In such a case, it is understood that compartment 24a would be dimensioned for storing such a form of the adjunctive medication.

Figure 4:
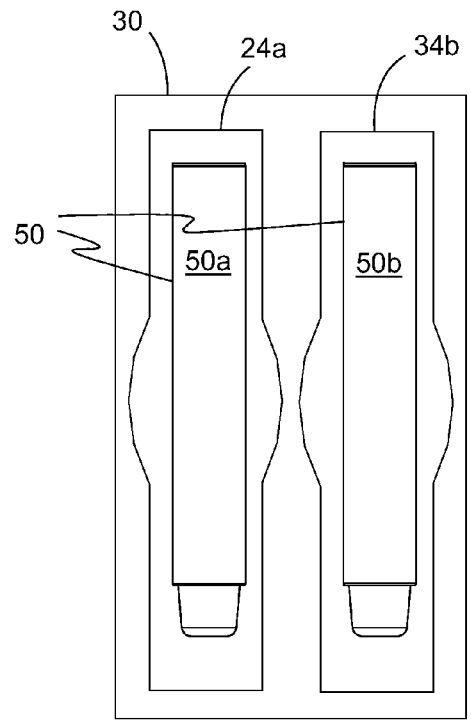
FIG. 4 is a top view of FIG. 1 showing only the upper compartments of the container.

FIG. 4 is a top view of removable upper tray 30. It is contemplated that upper tray 30 may be a fixed component of container 20 while lower tray 22 is removable. No matter the structural configuration, it is critical to the invention that a user can only access the first-line treatment medication 50 and administer such medication before accessing the second-line treatment medication 60. Upper tray 30 has upper compartments 34a, 34b where each compartment contains first-line treatment medication 50 that is an epinephrine injector pen or epinephrine-containing syringe. It is noted that container sealing cover 40 may be composed of multiple container sealing members or may be scored so that only one of the upper compartments 34a, 34b is opened at a time.

Figure 5:
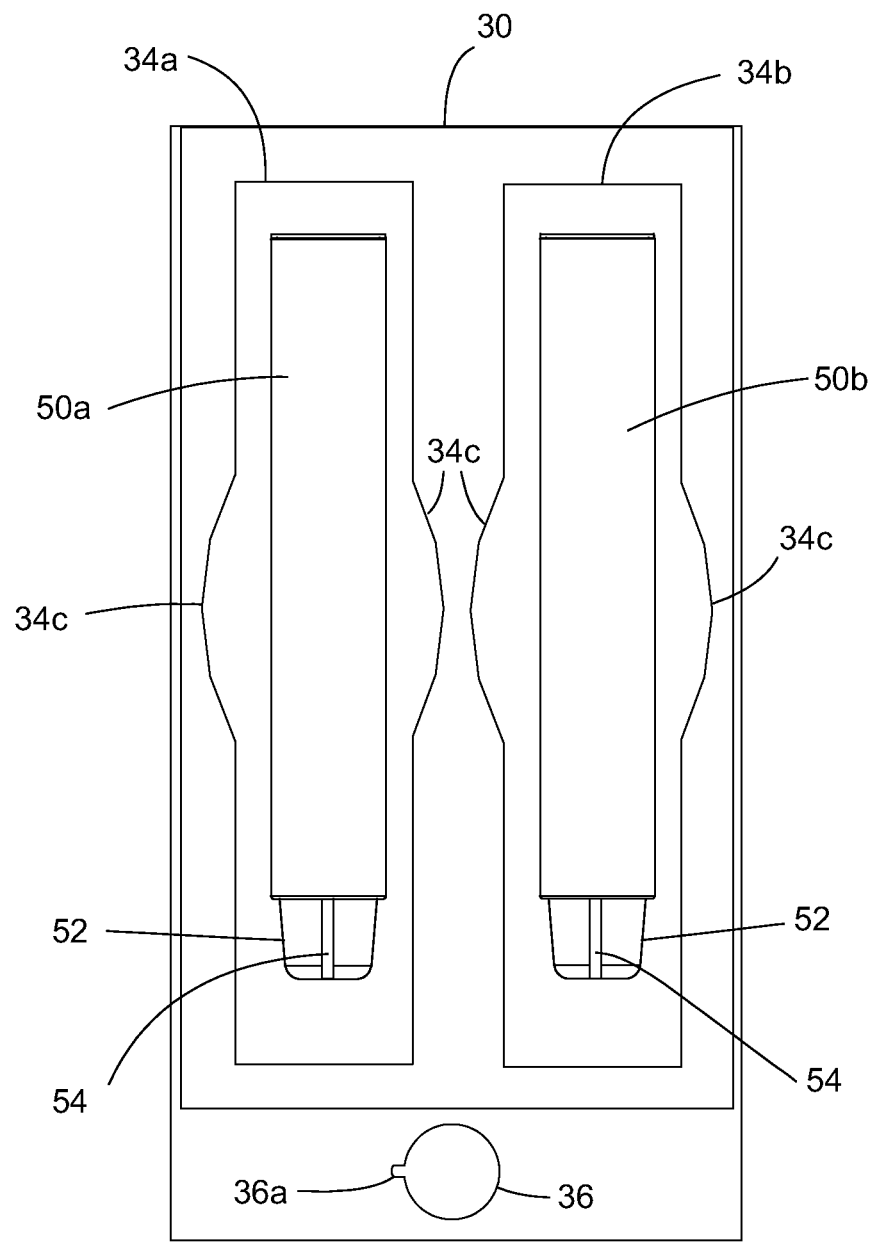
FIG. 5 is a top planar view of another embodiment of the upper compartments showing one embodiment of a keyed access to the lower compartments.

FIG. 5 is another embodiment of upper tray 30 of the present invention. In this embodiment, an injecting end 52 of the epinephrine injector includes a key 54. Upper tray 30 has a keyhole 36 with a keyway 36a shaped to receive injecting end 52 and key 54 in order to release a latch mechanism (not shown) thereby releasing upper tray 30 from container 20 and allowing a user access to the second-line treatment medications 60. It is understood that the key 54 may be at the opposite end of injector end 52 or may be a separate component located in a secondary compartment (not shown) in upper tray 30 below first-line treatment medication 50. It is further understood that the key and keyway positions may be reversed, or have other configurations, may be mechanical or electro-mechanical or other technology for accessing the second-line treatment medication 60. In fact, any configuration that forces a user to access and use the first-line treatment medication 50 before the second-line treatment medication 60 is contemplated by the present invention and is a part of the scope of the present invention. Upper tray 30 in this embodiment also includes contoured compartments that have side portions 34c of compartments 34a and 34b. Side portions 34c provide sufficient space to allow fingers to grasp the epinephrine injectors 50a, 50b with ease.

For example, either end of the epinephrine injector may result in a different shape after use where the shape forms the key that fits the keyhole to release the upper tray 30 to allow removal of upper tray 30 and access to second-line treatment medications 60. Alternatively, the act of using the epinephrine auto-injector creates an electrical or magnetic or electro-mechanical, or electromagnetic property in the injector that is used to release a holding mechanism so that upper tray 30 is removable from container 20 thereby allowing access to second-line treatment medications 60 only after first-line medication 50 is used.

Figure 6:
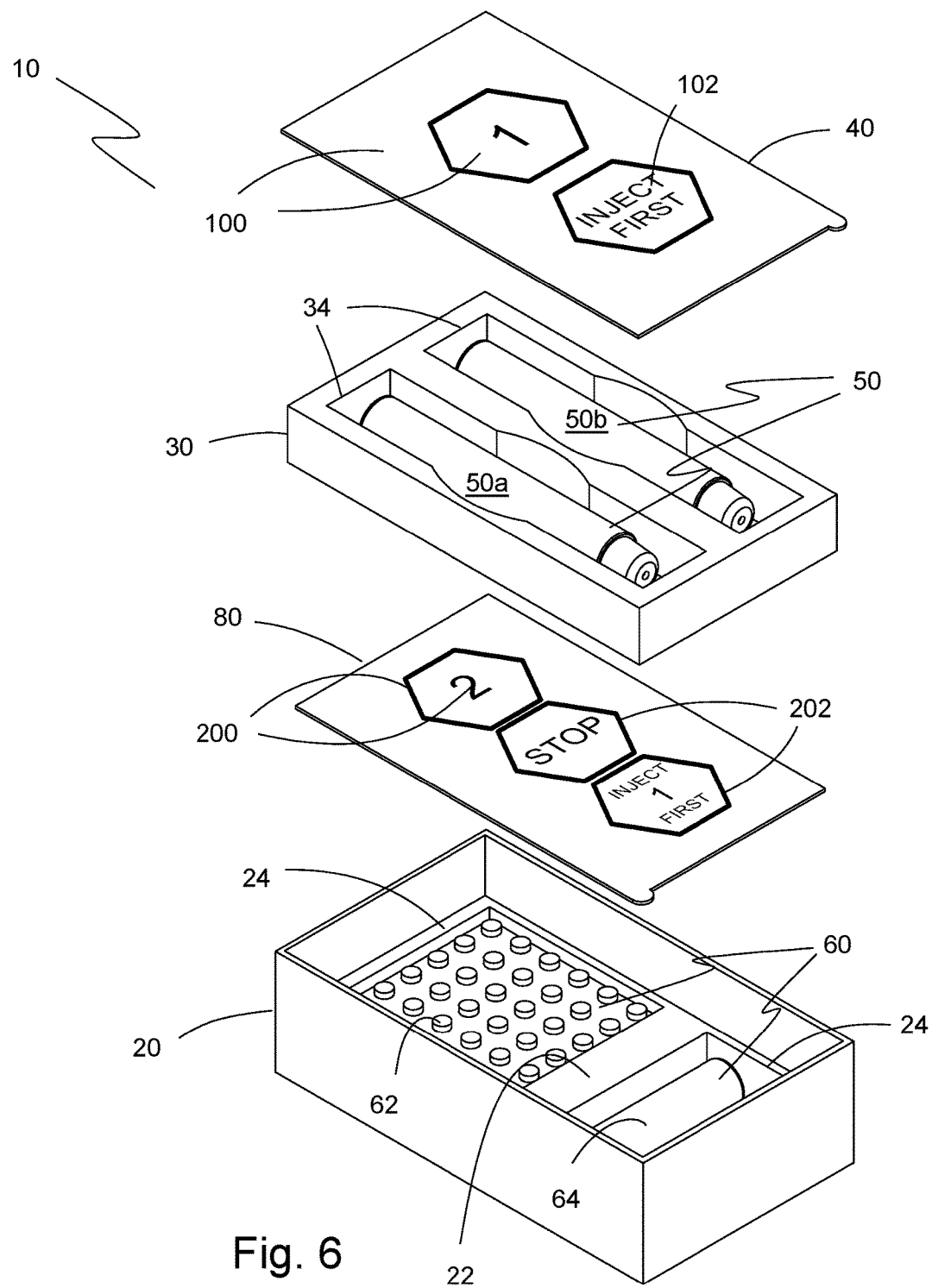
FIG. 6 is a perspective view of the embodiment with a removable tray showing indicia and/or warnings for the proper ordered administration of the medications.

FIG. 6 illustrates another embodiment of the present invention where the intervening sealing member 80 or a top surface 23 of lower tray 22 (or both when sealing member 80 is included) has indicia 200 and/or warning 202 that first-line treatment medication 50 must be used and administered first before accessing and administering the second-line treatment medication 60. Indicia 200 and/or warning 202 are not visible to the user until upper tray 30 is removed. The sealing cover 40 or a top surface 33 of upper tray 30 (or both) also includes indicia 100 indicating use of the first-line treatment medication 50. Sealing cover 40 or top surface 33 may also include a warning 102 along with medication administration steps. The indicia 100 on the cover 40 includes a prominently displayed number one or the letter A or other designation that indicates the first-line treatment medication 50 is administered/used first. The indicia 200 on the intervening sealing member 80 or on the top surface 23

(or both when sealing member 80 is included) includes a prominently displayed number two or the letter B or other designation that indicates the second-line treatment medication 60 is administered/used only after the first-line treatment medication is administered/used. Indicia 200 may optionally include a warning 202 of the consequences not administering the first-line treatment medication 50.

Figure 7:
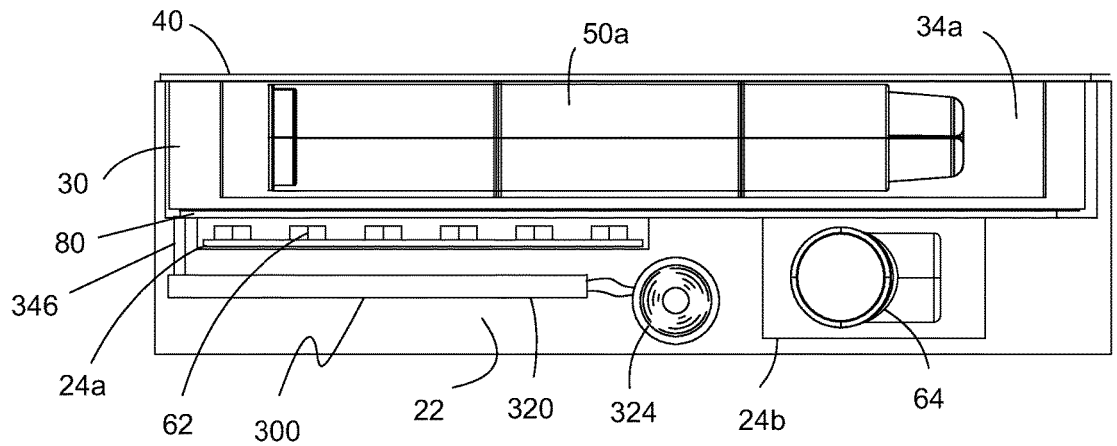
FIG. 7 is a side view of another embodiment of the present invention showing an audio message playback module incorporated within the container.
Figure 7A:
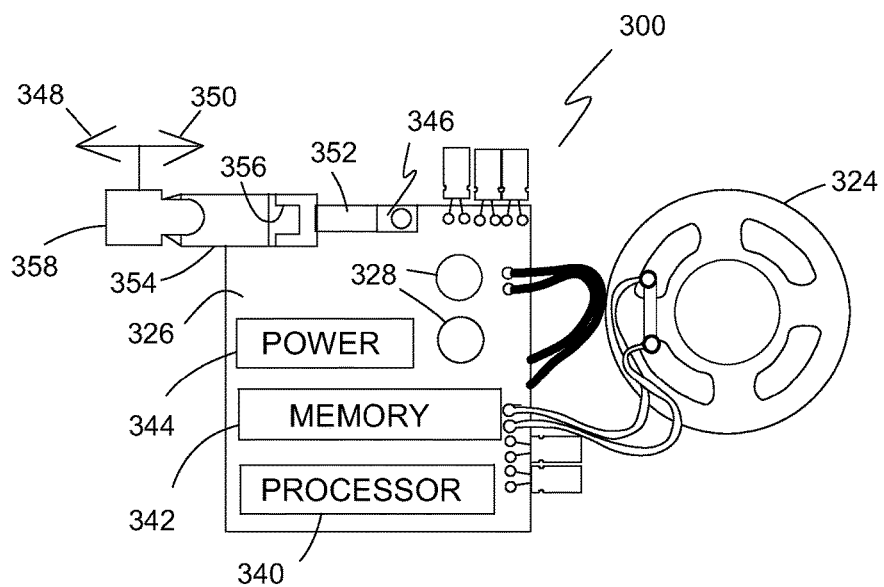
FIG. 7A is an illustration of one embodiment of the audio message playback module of FIG. 7.

FIGS. 7 and 7A illustrate still another embodiment of the present invention that incorporates an audio message playback module 300 disposed within container 20. Audio module 300 provides an audio warning that is activated when upper tray 30 is removed from container 20. The audio warning reminds the user that the first-line medication 50 must be administered first for proper treatment. The audio warning may also contain further warnings of the danger of administering only the second-line treatment medications 60. The audio warning module 300 may optionally be coupled with or without the inclusion of a second compartment sealing member 80.

The audio message playback module 300 is illustrated. The audio message playback module 300, for ease of manufacture and assembly of the allergic reaction treatment kit 10, may be provided on a carrier 320. The carrier 320 may be formed from a flat, rigid material, such as paper board, plastic or cardstock, that is able to hold components of the audio message playback module 300. The carrier 320 can then be adhered to inner surfaces of the container 20. Alternatively, the components of the audio message playback module 300 may be individually positioned inside the container 20 or mounted on a circuit board that is then mounted inside of container 20.

In one embodiment, the audio message playback module 300 includes a speaker 324, a circuit board 326, integrated circuits 328, a processor 340, a memory 342, a power supply 344, and a first switch 346. In the illustrated embodiment shown in FIG. 7A, the audio message playback module 300 includes two separate integrated circuits 328. The two separate integrated circuits 328 could be replaced by a single integrated circuit having the functionality discussed herein. Additionally, processor 340 may be incorporated into integrated circuits 328. Further, one integrated circuit with processor function may be used with a separate memory chip instead of, or in addition to, memory 342. In addition to the electrical components mentioned, which are coupled to the circuit board 326, other electrical components may be coupled with the circuit board as would be readily understood and appreciated by one of ordinary skill in the art.

The first switch 346 is implemented as a slide switch 346 that is opened 348 and closed 350, respectively. The slide switch 346 includes a contact arm 352 which is biased into a contact surface (not shown) on the circuit board 326. The slide switch 346 also includes a slide tab 354 that is movable between a first position (closed 350), where a portion of the slide tab 354 is intermediate the contact arm 352 and the contact surface of the circuit board 326, thereby creating an open circuit, and a second position (opened 348), illustrated in FIG. 7A, where the upper tray 30 or drawer 130 or folding tray 440, as the case may be, is in an open position and an aperture 356 in the slide tab 354 permits the contact arm 352 to abut the contact surface of the circuit board 326, thereby creating a closed circuit. A proximal end 358 of the slide tab 354 may be secured to a portion of the carrier 322 that is positioned to contact the upper tray 30 or drawer 130 or folding tray 440, as the case may be, whereby removal of the upper tray 30 or opening of the drawer 130 or opening of the folding tray 440 away from container 20, 120 (i.e., opening the container or removing upper tray 30 or opening the drawer 130) pulls the slide tab 354 out from between the contact arm 352 and the contact surface of the circuit board 326. When the upper tray 30 or drawer 130 or folding tray 440 is "opened," a first signal is provided to the processor 340 to indicate that the first switch 346 has been activated. The first signal may be generated by a container status detector within the audio message and playback module 300. In one embodiment, the audio message playback module 300 is continually powered by the power supply 344 in order to detect when the container 20 or upper tray 30 or drawer 130 or folding tray 440 has been opened 348 or closed 350. In alternative embodiments, either position 348, 350 of the first switch 346 or both positions may initiate power to the audio message playback module 300. In response to the first signal that the first switch 346 has been activated, the processor 340 retrieves a first sound recording from the memory 342 within the audio message playback module 300. The first sound recording is then played from the speaker 324. Additionally, a timing component may be used to delay the playback of the first sound recording. For example, the timing component may delay the playing of the first sound recording for 15 seconds after the container 20 or upper tray 30 or drawer 122 or folding tray 440 has been opened 348. The timing component may be within the processor 340. Alternatively, the timing component may be used to repeat playing of the first sound recording a predefined number of times.

It is also contemplated that the audio module 300 may also include an Internet-enabled component for accessing the internet along with the appropriate circuitry, all as is well known by the skilled artisan, for purposes as described in this specification. For example in an anaphylaxis event, the container may have an automatic telecommunication capability when opened to (a) immediately communicate with a call center to provide the anaphylaxis sufferer with medical counseling (as the patient may not recall their doctor's office instructions), (b) communicate to the anaphylaxis sufferer the location of the closest emergency room (possibly directing a rescue squad), and (c) direct the user to another epinephrine device in a pharmacy or nearby patient carrying an epinephrine device, if necessary, and (d) communicate directly to the patient's physician and patient portal tied to the patient's electronic medical record or to the electronic medical record itself.

Figure 8:
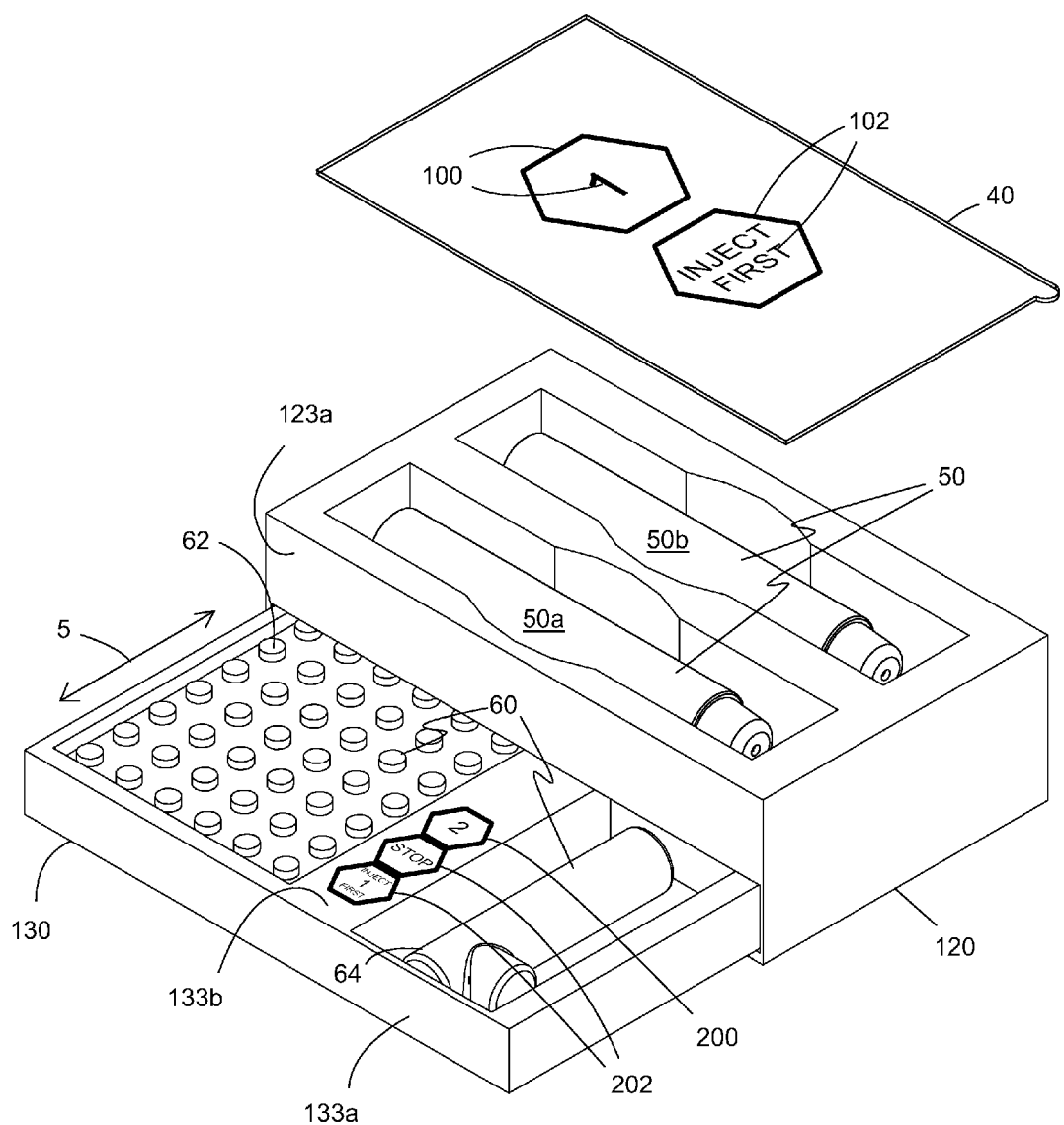
FIG. 8 is a perspective view of one embodiment of the present invention showing a container with a drawer.

FIG. 8 illustrates yet another embodiment of the present invention that incorporates a drawer 130 that slides in and out of container 120 (as indicated by arrow 5) for containing second-line medication 60. In this embodiment as in the removable tray embodiment, there may be optionally included a second compartment sealing member 80 (not shown for clarity reasons) that retains second-line medication 60 within draw 130 or that retains draw 130 in a closed position within container 120 where sealing member 80 must be removed to access the contents of draw 130. In the illustrated embodiment of FIG. 8, drawer 130 has integrally formed thereon indicia 200 and/or warning 202 that first-line treatment medication 50 must be used and administered first before accessing and administering the second-line treatment medication 60. Alternatively, this embodiment may incorporate a sealing member 80 over the second-line medication 60 that contains the indicia 200 and/or warning 202. In yet another alternative, this embodiment may incorporate an audio module 300 disposed within container 120 alone without sealing member 80 or in combination with sealing member 80. Audio module 300 provides an audio warning that is activated when draw 130 is opened and/or removed from container 120. It is contemplated that indicia 200 and/or warning 202 may be integrally formed onto one or more of a front outside surface 133*a* or a top surface 133*b* of draw 130 or a front outside surface of 123*a* of container 120. It should be understood that in the packaged state, drawer 130 is closed and inside of container 120 so that the only indicia visible is indicia 100 and/or warning 102 on first compartment sealing member 40 or on a top surface 123*a* of container 120. Indicia 200 and/or warning 202 are not visible until drawer 130 or the container is opened.

Figure 9:
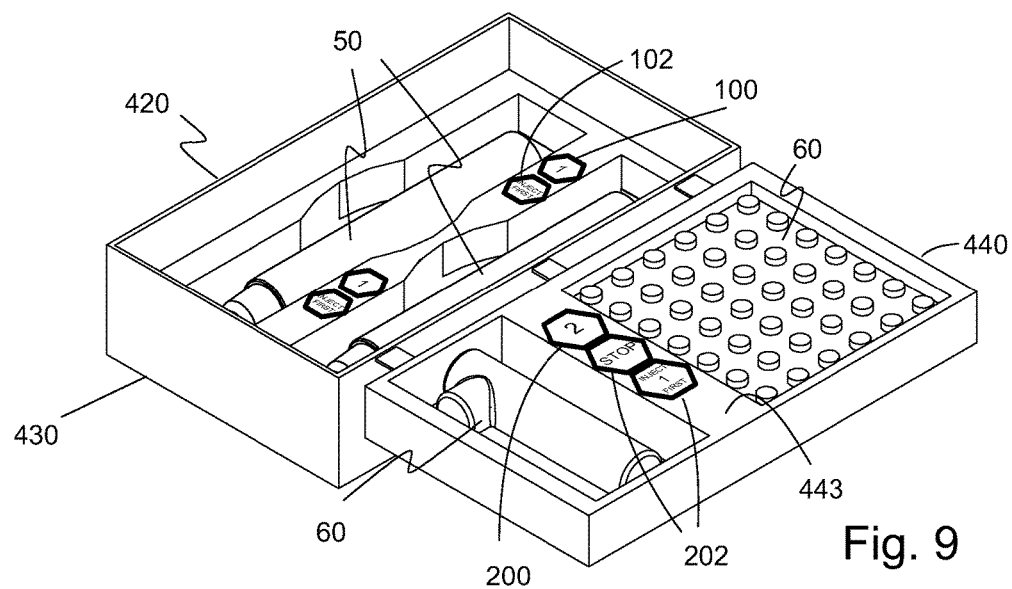
FIG. 9 is a perspective view of the present invention showing a container with a single fold-out tray.
Figure 9A:
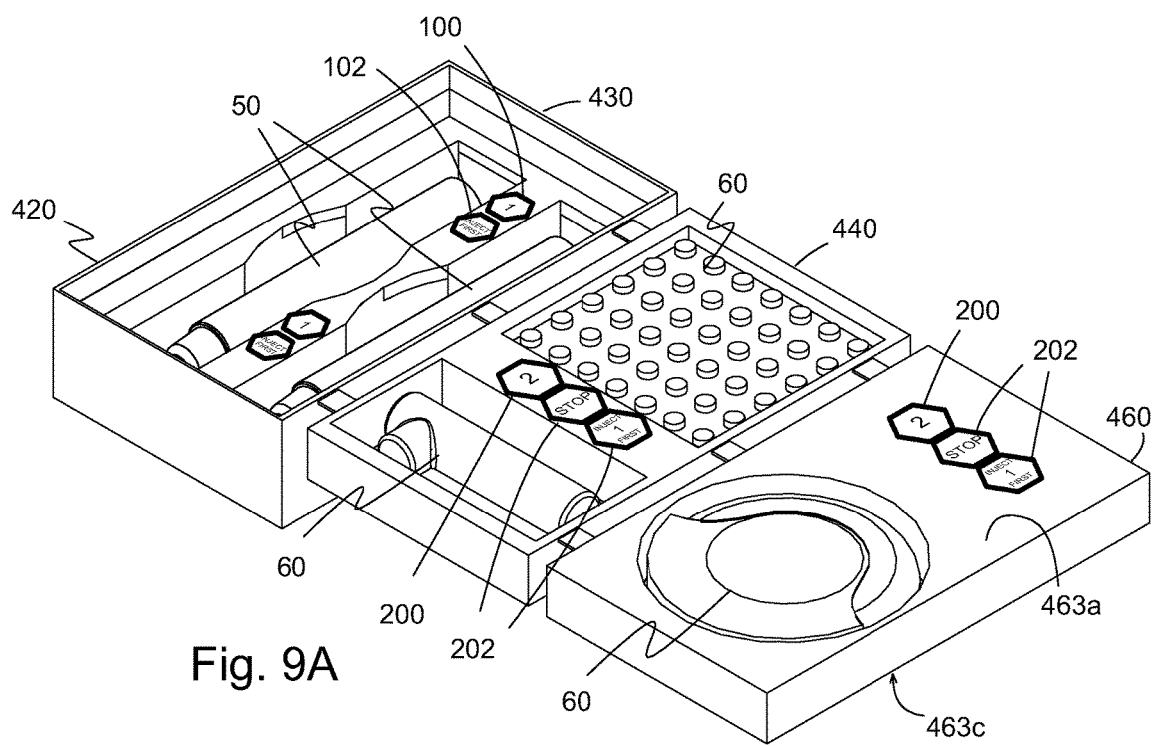
FIG. 9A is a perspective view of the present invention showing a container with a plurality of fold-out trays.
Figure 9B:
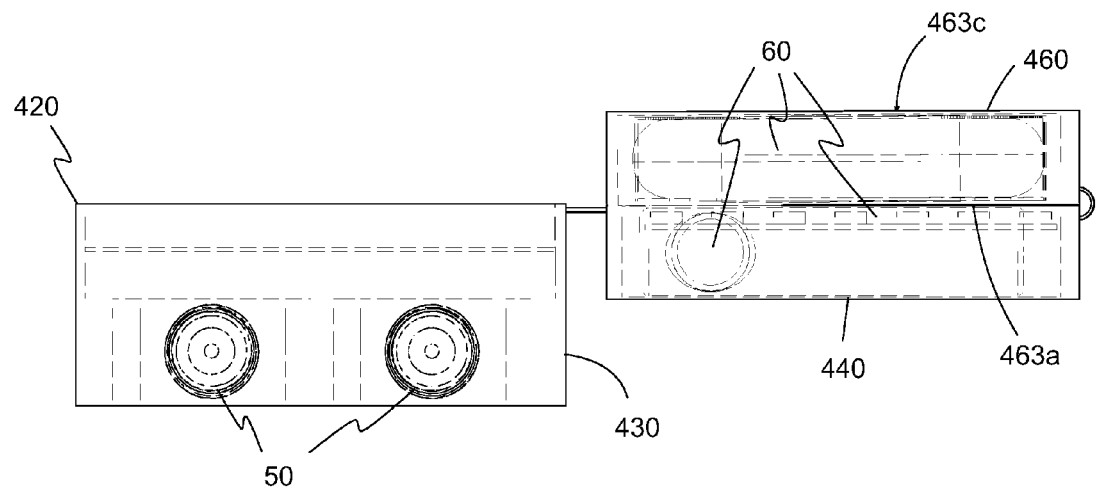
FIG. 9B is an end view of the present invention of FIG. 9A showing the container in a partially opened/closed state where one fold-out tray disposed onto a second fold-out tray.
Figure 9C:
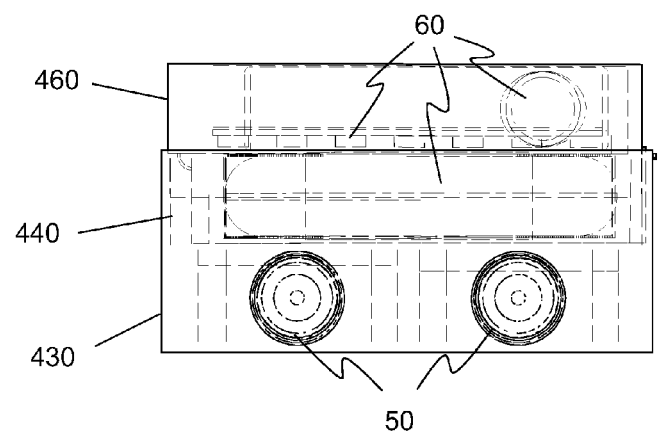
FIG. 9C is an end view of the present invention of FIG. 9A showing the container in a completely closed state where both fold-out trays are disposed within the base compartment of the container.
Figure 9D:
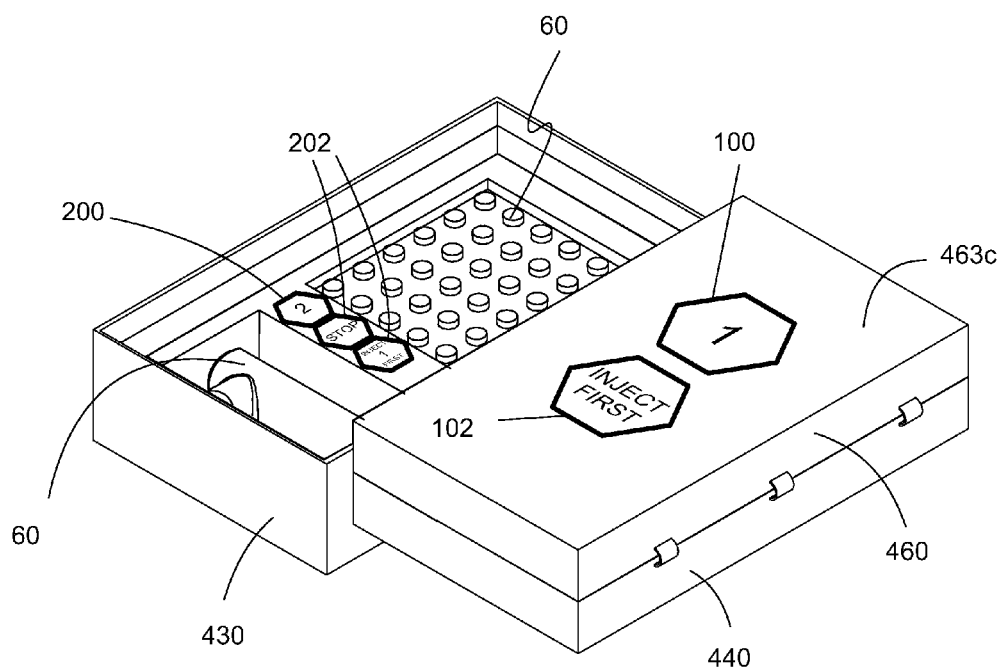
FIG. 9D is a perspective view of the fold-out container of FIG. 9A where the first-line medication is in one of the fold-out trays.

FIG. 9 illustrates yet another embodiment of the present invention that incorporates a folding container 420. Container 420 includes a base compartment 430 and a folding tray 440. Base compartment 430 contains the first-line treatment medication 50 and the folding tray 440 contains the second-line treatment medications 60. As with previously discussed embodiments, base compartment 430 contains one or more medications for the first-line treatment medication 50 and may or may not include a sealing cover 40 (not shown). Folding tray 440 includes an intervening sealing member 80 (not shown for clarity) or other structure formed within folding tray 440 that retains second-line treatment medications 50 in folding tray 440 until withdrawn by a user. A top surface 443 of folding tray 440 has indicia 200 and/or warning 202 that first-line treatment medication 50 must be used and administered first before accessing and administering the second-line treatment medication 60. If sealing member 80 is included, either sealing member 80 or top surface 443 or both may include indicia 200 and/or warning 202. Likewise, a top surface 433 of base compartment 430 has indicia 100 and/or warning 102 that first-line treatment medication 50 must be used and administered first before accessing the second-line treatment medication 60. If sealing member 40 is included, either sealing member 40 or top surface 433 or both may include indicia 100 and/or warning 102. As previously describe, audio module 300 may be included in folding container 420 in place of sealing member 80 and/or indicia 200 and/or warning 202 or together with one or more of sealing member 80 and/or indicia 200 and/or warning 202. Audio module 300 would be activated when folding tray 440 is opened from its folded position within base compartment 430. Audio module 300 may be included in any one of base compartment 430, folding tray 440 or folding tray 460. FIG. 9A illustrates a trifold container in an open position where there is a second folding tray 460. Second folding tray 460 also contains other second-line medications 60 such as, for example, dry powder or aerosolized inhalable epinephrine or inhalable steroids. FIG. 9B illustrates an end view of container 420 in a partially closed orientation with folding tray 440 folded onto folding tray 430. FIG. 9C illustrates container 420 in a closed orientation with folding tray 430 and folding tray 440. It is contemplated that the location of first-line medication 50 and second-line medication 60 may be changed such that first-line medication 50 is in folding tray 440 or folding tray 460 and second-line medication 60 is in the other folding tray and the base compartment 430, as the case may be. It is also understood that indicia 100, 200 and/or warnings 102, 202, respectively, would be appropriately located. For example as shown in FIG. 9D, if folding tray 460 retained first-line medication 50, the indicia 100 and/or warning 102 would be located on an outside bottom 463*c* as well as on a top surface 463*a* of folding tray 460.

The separation between trays (whether upper or lower or side-by-side or separated by other means), whereby one tray contains epinephrine while the other tray contains the adjunctive medications, can be distinguished not just by labeling but also by verbal instructions as part of the kit ("talking" instructions via various technologies) in order to reinforce the use of epinephrine. In order to further reinforce the use of epinephrine as the primary therapy, the "talking" instructions can be designed when the second tray is opened to remind the user of epinephrine's first-line indications for use and the need to proceed to the nearest hospital emergency room whether or not adrenalin was given. It is further contemplated that the removable tray embodiment and the drawer embodiment may include a plurality of removable trays or a plurality of drawers as desired to accommodate the second-line medications.

In still another embodiment of the present invention but not shown in the figures, the allergic reaction treatment kit 10 optionally includes automatic telecommunication capability when opened to (a) immediately communicate with a call center to provide the anaphylaxis sufferer with medical counseling (as the patient may not recall their doctor's office instructions), (b) communicate to the anaphylaxis sufferer the location of the closest emergency room (possibly directing a rescue squad), and (c) direct the user to another epinephrine device in a pharmacy or to a nearby patient carrying an epinephrine device, if necessary, and (d) communicate directly to the patient's physician and patient portal tied to the patient's electronic medical record or to the electronic medical record itself.

This same communication system can be added to a medical alert bracelet or other means of identifying an anaphylaxis sufferer and their specific allergies.

It is contemplated that allergic reaction treatment kit 10 may include medications either not currently utilized as ancillary medications but may be included at a later time or may be included as a result of newer guidelines being promulgated for treatment of allergic reactions as well as difficult-to-manage respiratory diseases.

Adjunctive/ancillary medications can include, but are not limited to, inhalers which provide immediate relief from asthma symptoms or upper airway spasm and constriction, antihistamines of different types to relieve hives, swelling, and itchiness as well as stabilize blood pressure, and anti-inflammatory medications such as prednisone to address the possibility of a delayed-onset allergic reaction. Other medications, even those not yet invented, to address the immediate, life-threatening symptoms associated with anaphylaxis are envisioned. Educational and communication technologies to locate the closest emergency room or nearest epinephrine syringe and to communicate instructions to utilize epinephrine when symptoms of anaphylaxis or difficult-to-manage respiratory symptoms occur can be incorporated.

Other embodiments involving other arrays of treatment regimens that require a specific order of use may also be used with the present invention. For example, treatment regimens and kits for other conditions such as pain, allergy, asthma, diabetes, heart failure management, and opioid overdose (with naloxone as an example of first-line therapy), and not just for anaphylaxis. As one example, an acute asthma emergency package focused on the immediate use of injected epinephrine or inhaled beta agonists and/or inhaled anticholinergics (delivered by metered-dose inhalers or by nebulization devices) can be instructed as first-line therapy with oral glucocorticoids (such as prednisone or methylprednisolone) and leukotriene receptor antagonists (such as montelukast or zafirlukast) as adjunctive medications.

Another example where the order of use is important is a treatment regimen requiring a specific ordering of medication use, such as the use of Afrin®, saline, and an inhaled nasal steroid for nasal congestion. Afrin® is first used to open the nasal passageways by decongesting the mucus membranes of the nose. Saline is then used to clear the mucus and debris from the nose in preparation for the inhaled nasal steroid, the definitive treatment that will reduce the inflammation in the mucus membranes of the nose, which is the root cause of the nasal congestion. All too often patients use saline after, not before, the inhaled nasal steroid, thereby washing out the nasal steroid. Alternative kits can be designed around medication regimens for postprandial management of diabetes with inhaled or injected insulin and an oral tablet as adjunctive therapy.

The present invention is particularly useful for any treatment regimens where the order of use of the medications is important to the successful outcome of treatment.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A medication treatment kit to ensure administration of medications in proper order for a treatment protocol requiring that the medications be taken in a particular order, the kit comprising:
   a container;
   a lower tray located in a bottom of the container, the lower tray having one or more compartments wherein the one or more compartments contain a second-line treatment medication for a particular treatment protocol wherein the second-line treatment medication is not to be taken first by the user;
   an upper tray located on top of the lower tray, the upper tray having one or more compartments wherein the one or more compartments contain a first-line treatment medication for the particular treatment protocol wherein the first-line treatment medication is required to be taken first by the user, and wherein the upper tray and the lower tray are removable from each other;
   wherein the second-line treatment medication is inaccessible without first accessing the upper tray and the first-line treatment medication whereby the kit is configured to ensure the first-line treatment medication is used first and to ensure the medications are administered in proper order for the treatment protocol; and
   wherein there are no other medications located side-by-side relative to the first-line medication and where only the first-line medication is initially presented.

2. The medication treatment kit of claim 1 further comprising a removable intervening member disposed on a top surface of the lower tray such that the second-line treatment medication in the lower tray is inaccessible without first:
   a) accessing the upper tray and the first-line treatment medication, and
   b) removing the intervening member.

3. The medication treatment kit of claim 1 further comprising a removable cover disposed on one of the upper tray or the container.

4. The medication treatment kit of claim 1 further comprising indicia on an intervening member and a cover wherein the indicia indicates the order of use of the first-line treatment medication and the second-line treatment medication and wherein the indicia on the intervening member is non-viewable until the upper tray is removed from the container.

5. The medication treatment kit of claim 4 wherein the intervening member further includes a warning about the order of use of the first-line treatment medication.

6. The medication treatment kit of claim 1 further comprising an audio module disposed within the container and operable when the upper tray is removed from the container wherein the audio module emits an audible signal indicating the order of use of the first-line treatment medication and the second-line treatment medication.

7. The medication treatment kit of claim 1 wherein the second-line treatment medication is one or more of an antihistamine, a steroid, an inhalable epinephrine, a metered dose inhaler, a dry powder inhaler, and a aerosolized inhaler.

8. The medication treatment kit of claim 1 wherein the first-line treatment medication is an injectable epinephrine for treating the user having an allergic reaction and wherein the second-line treatment medication is used as an adjunctive medication to treat a user having an allergic reaction.

9. A medication treatment kit to ensure administration of medications in proper order for a treatment protocol requiring the medications be taken in a particular order, the kit comprising:
   a container having a lower portion and an upper portion;
   a drawer in the lower portion of the container wherein the drawer is slidable between a closed position and an open position, the drawer having one or more compartments wherein the one or more compartments contain a second-line treatment medication for a particular treatment protocol wherein the second-line treatment medication is not to be taken first by the user;
   an upper tray located in the upper portion of the container, the upper tray having one or more compartments wherein the one or more compartments contain a first-line treatment medication for the particular treatment protocol wherein the first-line treatment medication is required to be taken first by the user;
   indicia on an outer surface of the drawer and on a top surface of the upper tray that indicates the order of use of the first-line treatment medication and the second-line treatment medication and is configured to ensure the first-line treatment medication is used first and to ensure the medications are administered in proper order for the treatment protocol,
   wherein no other medications are located side-by-side relative to the first-line medication and where only the first-line medication is initially presented.

10. The medication treatment kit of claim 9 further comprising an intervening member disposed on at least a portion of the outer surface of the drawer and on at least an outer surface of the container, the intervening member configured to prevent the second-line treatment medication in the drawer from being accessible.

11. The medication treatment kit of claim 9 wherein the intervening member has indicia indicating the drawer contains second-line treatment medication and further indicates the order of use of the first-line treatment medication and the second-line treatment medication.

12. The medication treatment kit of claim 9 further comprising an audio module disposed within the container and operable when the drawer is moved from the closed position to the open position wherein the audio module emits an audible signal indicating the order of use of the first-line treatment medication and the second-line treatment medication.

13. An medication treatment kit of claim 9 wherein the wherein the second-line treatment medication is one or more of an antihistamine, a steroid, an inhalable epinephrine, a metered dose inhaler, a dry powder inhaler, and a aerosolized inhaler.

14. The medication treatment kit of claim 9 wherein the first-line treatment medication is an injectable epinephrine for treating the user having an allergic reaction and wherein the second-line treatment medication is used as an adjunctive medication to treat a user having an allergic reaction.

* * * * *